US012005420B2

(12) United States Patent
Perez-Pellitero et al.

(10) Patent No.: US 12,005,420 B2
(45) Date of Patent: Jun. 11, 2024

(54) ZEOLITIC ADSORBENT FOR THE SEPARATION OF HYDROCARBON ISOMERS

(71) Applicant: Arkema France, Colombes (FR)

(72) Inventors: Javier Perez-Pellitero, Rueil-Malmaison (FR); Ludivine Bouvier, Lacq (FR); Maria Manko, Rueil-Malmaison (FR)

(73) Assignee: Arkema France, Colombes (FR)

( * ) Notice: Subject to any disclaimer, the term of this patent is extended or adjusted under 35 U.S.C. 154(b) by 192 days.

(21) Appl. No.: 17/787,351

(22) PCT Filed: Dec. 18, 2020

(86) PCT No.: PCT/FR2020/052532
§ 371 (c)(1),
(2) Date: Jun. 20, 2022

(87) PCT Pub. No.: WO2021/123664
PCT Pub. Date: Jun. 24, 2021

(65) Prior Publication Data
US 2023/0023245 A1 Jan. 26, 2023

(30) Foreign Application Priority Data

Dec. 20, 2019 (FR) ...................................... 1915324

(51) Int. Cl.
| | |
|---|---|
| *B01J 20/28* | (2006.01) |
| *B01D 15/18* | (2006.01) |
| *B01J 20/18* | (2006.01) |
| *B01J 20/30* | (2006.01) |
| *B01J 35/30* | (2024.01) |
| *B01J 37/00* | (2006.01) |
| *C07C 7/13* | (2006.01) |
| *C07C 15/02* | (2006.01) |
| *C07C 15/04* | (2006.01) |
| *C07C 15/06* | (2006.01) |
| *C07C 15/08* | (2006.01) |
| *C07C 29/76* | (2006.01) |
| *C07C 37/82* | (2006.01) |
| *C07C 39/07* | (2006.01) |
| *C07C 201/16* | (2006.01) |
| *C07C 205/06* | (2006.01) |
| *C07C 211/50* | (2006.01) |

(52) U.S. Cl.
CPC .......... *B01J 20/18* (2013.01); *B01D 15/1821* (2013.01); *B01J 20/28004* (2013.01); *B01J 20/28011* (2013.01); *B01J 20/2803* (2013.01); *B01J 20/3028* (2013.01); *B01J 35/30* (2024.01); *B01J 37/0009* (2013.01); *C07C 7/13* (2013.01); *C07C 15/02* (2013.01); *C07C 15/04* (2013.01); *C07C 15/06* (2013.01); *C07C 15/08* (2013.01); *C07C 29/76* (2013.01); *C07C 37/82* (2013.01); *C07C 39/07* (2013.01); *B01D 2253/108* (2013.01); *B01D 2253/1085* (2013.01); *C07C 201/16* (2013.01); *C07C 205/06* (2013.01); *C07C 211/50* (2013.01)

(58) Field of Classification Search
CPC .. B01J 20/18; B01J 20/2803; B01J 20/28004; B01J 20/28011; B01J 20/28042; B01J 20/3028; B01J 20/3078; B01J 20/3085; B01J 35/00; B01J 35/023; B01J 35/30; B01J 37/0009; Y02P 20/52; B01D 15/1821; B01D 2253/108; B01D 2253/1085; C07C 7/13; C07C 15/02; C07C 15/04; C07C 15/06; C07C 15/08; C07C 37/82; C07C 29/76; C07C 39/07; C07C 205/06; C07C 201/16; C07C 211/50
USPC ........ 502/400, 407, 411, 414; 585/804, 820, 585/825, 828, 831; 208/310 R, 310 Z
See application file for complete search history.

(56) References Cited

U.S. PATENT DOCUMENTS

| | | | |
|---|---|---|---|
| 2,985,589 | A | 5/1961 | Broughton et al. |
| 4,306,107 | A | 12/1981 | Broughton |
| 4,326,092 | A | 4/1982 | Neuzil |
| 5,382,747 | A | 1/1995 | Kulprathipanja |
| 5,900,523 | A | 5/1999 | Kulprathipanja |
| 6,136,198 | A | 10/2000 | Adam et al. |
| 7,208,651 | B2 | 4/2007 | Frey |

(Continued)

FOREIGN PATENT DOCUMENTS

| | | |
|---|---|---|
| FR | 2889698 A1 | 2/2007 |
| FR | 2889699 A1 | 2/2007 |

(Continued)

OTHER PUBLICATIONS

Breck, D., "Zeolites Molecular Sieves", John Wiley & Sons, 1973, 4 pages.

(Continued)

*Primary Examiner* — Elizabeth D Wood
(74) *Attorney, Agent, or Firm* — Buchanan Ingersoll & Rooney PC

(57) ABSTRACT

The present invention concerns a zeolitic adsorbent agglomerate comprising at least one zeolite of faujasite type comprising sodium and/or lithium and/or calcium, and/or barium and/or potassium, of porosity between 25% and 45%, and having a standard deviation σ of crystal size distribution in said agglomerate of less than 0.30 µm. The invention also concerns the use of the zeolitic adsorbent agglomerate to separate hydrocarbon mixtures, and the process to separate hydrocarbon mixtures using said zeolitic adsorbent agglomerate.

14 Claims, No Drawings

(56) References Cited

U.S. PATENT DOCUMENTS

| | | |
|---|---|---|
| 7,468,468 B2 | 12/2008 | Leflaive et al. |
| 7,728,187 B2 | 6/2010 | Kulprathipanja |
| 8,530,367 B2 | 9/2013 | Bouvier et al. |
| 9,061,918 B2 | 6/2015 | Bouvier et al. |
| 9,447,001 B2 | 9/2016 | Etienne et al. |
| 10,071,914 B2 | 9/2018 | Nicolas et al. |
| 10,125,064 B2 | 11/2018 | Laroche et al. |
| 10,722,862 B2 | 7/2020 | Bouvier et al. |
| 10,940,458 B2 | 3/2021 | Laroche et al. |
| 2007/0224113 A1 | 9/2007 | Willis et al. |
| 2009/0326308 A1 | 12/2009 | Kulprathipanja |
| 2017/0217858 A1* | 8/2017 | Laroche ............ B01J 20/28092 |
| 2023/0219059 A1* | 7/2023 | Perez-Pellitero ......... C07C 7/11 502/64 |

FOREIGN PATENT DOCUMENTS

| | | |
|---|---|---|
| FR | 2998808 A1 | 6/2014 |
| TW | 201107032 A | 3/2011 |
| WO | 2008009845 A1 | 1/2008 |
| WO | 2009081022 A2 | 7/2009 |
| WO | 2014090771 A1 | 6/2014 |
| WO | 2018002174 A1 | 1/2018 |

OTHER PUBLICATIONS

French Search Report for French Application No. 1915324, dated Dec. 20, 2019, 10 pages.

International Search Report and Written Opinion for International Application No. PCT/FR2020/052532, dated Mar. 30, 2021, 9 pages.

* cited by examiner

ZEOLITIC ADSORBENT FOR THE SEPARATION OF HYDROCARBON ISOMERS

CROSS-REFERENCE TO RELATED APPLICATIONS

This application is a 371 filing of International Application No. PCT/FR2020/052532, filed Dec. 18, 2020, which claims priority to French Application No. 1915324 filed Dec. 20, 2019, the disclosures of these applications being incorporated herein by reference in their entireties for all purposes.

FIELD OF THE INVENTION

The invention concerns the field of zeolitic adsorbents in the form of agglomerates comprising zeolite of faujasite type, for the separation of gaseous or liquid mixtures of aromatic hydrocarbons, and more particularly concerns processes for separating xylenes and in particular processes for separating meta-xylene with improved productivity.

The present invention further concerns a process for separating gaseous or liquid mixtures of isomers with improved productivity, and more particularly a process for separating isomers of xylene with improved productivity for the production of highly pure meta-xylene from a feed of aromatic hydrocarbons containing isomers having 8 carbon atoms.

BACKGROUND OF THE INVENTION

The use of zeolitic adsorbents composed of Faujasite zeolites (FAU) of type Y for the selective adsorption of meta-xylene in a mixture of aromatic hydrocarbons is well known in the prior art.

For example, U.S. Pat. Nos. 4,306,107, 4,326,092, 5,382,747, 5,900,523 and U.S. Pat. No. 7,728,187 as well as FR2889698 and FR2889699 show that zeolitic adsorbents comprising aluminosilicates containing sodium or containing sodium and lithium, are efficient for the separation of meta-xylene present in C8 aromatic fractions (fractions containing aromatic hydrocarbons having 8 carbon atoms). Patent TW201107032 describes zeolite Y adsorbents exchanged with silver or copper having improved transfer and selectivity properties for the recovery of meta-xylene.

The adsorbents described in U.S. Pat. No. 5,900,523 are used as adsorption agents in liquid phase processes, preferably of simulated counter-current type, similar to those described in U.S. Pat. No. 2,985,589 and which inter alia apply to C8 aromatic fractions.

It is the objective of the invention to improve the productivity of existing processes for preparing meta-xylene and in particular liquid phase processes, preferably of simulated counter-current type for separating isomers of xylene from C8 aromatic feeds. It has been surprisingly observed that this productivity can be improved through a judicious choice of the characteristics of the zeolitic adsorbent agglomerates used in processes of this type.

Separation in a simulated moving bed is to be construed herein in its broad meaning i.e. it may either concern a simulated counter-current moving bed or a simulated co-current moving bed, or it may relate to a so-called "Varicol" process. The Varicol process proposed by Ludemann-Hombourger (O. Ludemann-Hombourger, R. Nicoud, 2000) and later developed by Novasep, allows non-synchronized shifting of the inlet and outlet lines (Bailly, et al. 2004). The lengths of the four zones can be adjusted during a cycle by limiting the number of beds required to carry out separation.

The characteristic common to this family of processes is that the zeolitic adsorbent agglomerate (or more simply «solid adsorbent») is placed in a fixed bed, and the liquid streams in contact with the solid adsorbent are managed either by means of a set of «on-off» valves, or by means of a single complex valve known as a "rotary valve".

When the active element of the solid adsorbents used as adsorption agents in these processes is a zeolite, the latter obtained in crystal form is preferably used on industrial scale in the form of agglomerates. These zeolitic adsorbents agglomerated in the form of laminates, beads or extrudates, are generally composed of zeolite crystals, forming the active element with regard to adsorption, and of a binder intended to ensure the cohesion of the crystals in the form of agglomerates. This binder also imparts sufficient mechanical strength to the agglomerates to withstand the mechanical stresses to which they are subjected when used in operating units. These mechanical stresses are the cause of the formation of «fines», which lead to deteriorated performance throughout the operating time of the process.

The process for separating xylenes in a simulated moving bed (SMB) has undergone numerous technological improvements, in particular with respect to the liquid distributor plates, but relatively little progress concerning the intrinsic characteristics of the solid adsorbent.

Document U.S. Pat. No. 4,306,107 describes the use, as selective meta-xylene adsorbent, of a zeolite Y in which the exchangeable cation cites are occupied by sodium atoms. To obtain satisfactory meta-xylene selectivity, it is recommended to use a partially hydrated zeolite having loss on ignition at 950° C. of 2% to 7% by weight of the initial weight of the adsorbent. In this document, separation is recommended in a simulated moving bed process at a temperature of between 20° C. and 250° C. and at a pressure between atmospheric pressure and 3.5 MPa (35 bars), a value selected to maintain the feed in liquid form. Occupation of the zeolite exchangeable sites by sodium ions and activation to obtain the desired loss on ignition allow agglomerates to be obtained which, with regard to the adsorption of meta-xylene contained in C8 aromatic fractions, have improved properties of capacity and selectivity.

Adsorbents for the separation of xylenes having improved transfer properties for the separation of xylenes are described for example in international application WO2008009845 which describes zeolite X adsorbents having small crystals of size smaller than 1.7 μm, of Si/Al atomic ratio such that 1.15<Si/Al≤1.5, exchanged with barium, and optionally with potassium in international application WO2014090771 which describes agglomerated zeolitic adsorbents having optimized properties in particular for the separation of para-xylene from C8 aromatic fractions. These adsorbents exhibit maximum properties of para-xylene selectivity and mass transfer whilst having maximum mechanical strength associated with optimized adsorption capacity.

International application WO2018002174 proposes zeolitic adsorbents in the form of agglomerates having optimized properties for separating gaseous or liquid mixtures of isomers and more particularly for the separation of xylenes in gas or liquid phase and in particular of para-xylene from C8 aromatic fractions. The zeolitic adsorbents of the application in particular display maximum properties for para-xylene selectivity and mass transfer whilst having improved strength and high adsorbent capacity per volume of adsorbent, and are particularly suitable for use in a separation process of para-xylene in liquid phase, preferably of simulated counter-current type.

In particular, this application teaches that a strong increase in macroporosity and/or mesoporosity is not desirable, hence in particle porosity, since this porosity does not take part in adsorption capacity. Optimization of diffusing properties and adsorption capacities were obtained by specifically selecting both porosity and tortuosity factor.

Patent application US2009/0326308 describes a separation process using an adsorbent with low binder content and containing type X faujasite crystals of nanometric size, typically a mean size of less than 500 nm.

In a process for separating xylenes via adsorption in a simulated moving bed, the zeolitic adsorbent is contacted with the liquid feed stream (feed mixture) most often comprising mixtures of C8 hydrocarbons, and generally and most often mixtures of xylene isomers and more particularly mixtures of ortho-xylene, meta-xylene, para-xylene and ethylbenzene.

By using a zeolitic adsorbent containing zeolite of type Y faujasite structure exchanged with sodium or exchanged with sodium and lithium, the meta-xylene is adsorbed in the micropores of the zeolite, preferably in preference to all the other hydrocarbon compounds in the feed stream. The adsorbed phase in the zeolite micropores becomes enriched with meta-xylene compared with the initial mixture forming the feed stream. On the contrary, the liquid phase becomes enriched with compounds such as ortho-xylene, para-xylene and ethylbenzene in greater relative proportion than that characterizing the initial mixture forming the feed stream.

The liquid phase is drawn off from contact with the adsorbent thereby forming a stream of raffinate. The adsorbed phase, enriched with meta-xylene, is desorbed under the action of a flow of desorbent and drawn off from contact with the adsorbent thereby forming a stream of extract.

In the separation process of xylenes via adsorption in a simulated moving bed, the solid zeolitic adsorbent passes through one or two multi-stage columns to be contacted with the flow of liquid. A multi-stage column is a column composed of a multiplicity of plates arranged along a substantially vertical axis, each plate supporting a bed of particulate solid, and the different successive beds receiving the throughflow in series of the liquid or liquids used in the column. Between two successive beds there is a liquid distribution device feeding each bed of particulate solid.

In general, the operation of a column in a simulated moving bed can be described as follows:

A column comprises at least four zones and optionally five or six, each of these zones being composed of a certain number of successive beds, and each zone being defined by its position between an inlet line and an outlet line. Typically, a simulated counter-current unit (SCC) for the production of meta-xylene is fed with at least one feed F to be fractionated (feed mixtures of aromatic hydrocarbons composed of isomers having 8 carbon atoms) and a desorbent D sometimes called eluent, and from said unit at least one raffinate R is withdrawn containing the products of the feed that are least selectively adsorbed and desorbent, and an extract E containing the product of the feed that is most adsorbed and desorbent.

Other inlet and outlet lines can be added for rinsing the distribution circuits as described for example in U.S. Pat. No. 7,208,651. Since the addition of these additional rinsing flows in no way changes the operating principle of the SCC unit, for the sake of brevity we will not include these additional inlet and outlet lines in the description of the process of the invention.

The inlet and outlet lines are modified over time, shifted in the same direction by a value corresponding to one bed. Shifting of the different inlet or outlet lines can be simultaneous or non-simultaneous as taught in U.S. Pat. No. 6,136,198. The process according to this second operating mode is called Varicol.

Conventionally, 4 different chromatographic zones are defined in a column operating in simulated counter-current (SCC).

Zone 1: desorption zone of the most adsorbed product in the feed, positioned between injection of the desorbent D and withdrawal of the extract E.

Zone 2: desorption zone of the least selectively adsorbed products in the feed, positioned between withdrawal of the extract E and injection of the feed F to be fractionated.

Zone 3: adsorption zone of the most adsorbed product in the feed, positioned between injection of the feed and withdrawal of the raffinate R.

Zone 4: zone positioned between withdrawal of the raffinate R and injection of the desorbent D.

To increase the productivity of the separation process, the prior art teaches that one manner is to improve overall transfer into the zeolitic adsorbent agglomerate, and in particular by reducing the size of the crystals and/or the mean size of said agglomerates.

The prior art documents disclosing processes for pharmaceutical separation (Gomes et al., (2006), *Adsorption*, vol. 12, p. 375 sqq.) describe liquid phase chromatographic separation processes using agglomerates of size ranging from a few tens of micrometres up to 100 μm.

In these processes using adsorbents of very small size, the pressure drop ΔP is very high. For xylene separation processes, such levels of pressure drop ΔP are not frequent. It is nevertheless surprisingly observed that pressure drop ΔP is not a dimensioning criterion. It has particular impact on the thickness of the adsorber walls and on the power of operating units.

A further characteristic of the zeolitic adsorbent agglomerate is the rate of hydration of said agglomerate. Maintaining hydration of the zeolite at the desired value, for example loss on ignition less than or equal to 7% for zeolite Y, when used in a xylene separation process via adsorption in a simulated moving bed, is ensured by adding water to the feed and/or desorbent streams. The amount of water to be added for such levels of loss on ignition is such that the weight content of water in the hydrocarbon effluents (extract or raffinate streams) is most often between 0 ppm and 150 ppm, and more generally between 0 and 80 ppm when the adsorbent contains zeolite FAU-Y.

Nevertheless, it is generally always necessary to increase the productivity of the process.

Said zeolitic adsorbent materials of zeolite FAU-Y type, and in particular containing cations selected from among lithium, potassium, sodium, barium, calcium, and mixtures of two or more of the latter, could provide significant improvements in processes for separating xylenes present in the form of isomer mixtures in C8 aromatic hydrocarbon fractions, and in particular could largely improve the selective adsorption of meta-xylene in C8 aromatic hydrocarbon mixtures.

A first object of the present invention is therefore to propose a zeolitic adsorbent in the form of agglomerates having optimized properties for the separation of gaseous or liquid mixtures of isomers and more particularly for the separation of xylenes, in gas phase or liquid phase, and in particular for the separation of meta-xylene from C8 aromatic fractions. The zeolitic adsorbent agglomerates of the invention particularly display maximum properties of meta-xylene selectivity and mass transfer, whilst having high mechanical strength and adsorption capacity, and are particularly suitable for use in a liquid phase separation process of meta-xylene, preferably of simulated counter-current type.

For this purpose, the invention proposes an agglomerated adsorbent, preferably of faujasite zeolite having a Si/Al atomic ratio strictly higher than 1.50, advantageously between 1.50 and 6.50 limits excluded, the particle porosity of which is advantageously between 25% and 45%, allowing the production of meta-xylene of high purity with improved productivity, whilst avoiding degradation of performance over time. More specifically, the invention concerns a zeolitic agglomerated adsorbent comprising at least one faujasite zeolite of Si/Al atomic ratio strictly higher than 1.50, advantageously between 1.50 and 6.50 limits excluded, preferably between 2.00 and 6.00 limits included, more preferably between 2.00 and 4.00 limits included, and further preferably between 2.20 and 2.80 limits included, and wherein first the particle porosity is between 25% and 45%, preferably between 30% and 45%, more preferably between 32% and 45%, further preferably between 35% and 45%, and particularly advantageously between 36% and 45% limits included, and secondly in that the standard deviation σ of crystal size distribution in said agglomerate is less than 0.30 μm, preferably between 0.05 μm and 0.30 μm, more preferably between 0.05 μm and 0.28 μm, further preferably between 0.1 μm and 0.28 μm, most preferably between 0.1 μm and 0.25 μm, limits included.

SUMMARY OF THE INVENTION

Therefore, in a first aspect, the invention concerns an agglomerated zeolitic adsorbent comprising at least one faujasite zeolite of Si/Al atomic ratio strictly higher than 1.50, advantageously between 1.50 and 6.50 limits excluded, preferably between 2.00 and 6.00 limits included, more preferably between 2.00 and 4.00 limits included, and further preferably between 2.20 and 2.80 limits included, characterized in that the particle porosity of said adsorbent is between 25% and 45%, preferably between 30% and 45%, more preferably between 32% and 45%, further preferably between 35% and 45%, and particularly advantageously between 36% and 45% limits included, and in that the standard deviation a of crystal size distribution in said agglomerates is less than 0.30 μm, preferably between 0.05 μm and 0.30 μm, more preferably between 0.05 μm and 0.28 μm, further preferably between 0.1 μm and 0.28 μm, most preferably between 0.1 μm and 0.25 μm, limits included.

In one embodiment, the agglomerated zeolitic adsorbent of the invention comprises zeolite crystals of number-weighted mean diameter less than 1200 nm, preferably between 100 nm and 1200 nm, more preferably between 400 nm and 1200 nm, further preferably between 500 nm and 1200 nm, still further preferably between 550 nm and 1200 nm, and most advantageously between 600 nm and 1200 nm, limits included.

In another embodiment, the agglomerated zeolitic adsorbent of the invention is in the form of beads of mean diameter between 100 μm and 1000 μm, preferably between 100 μm and 600 μm, more preferably between 200 μm and 550 μm, limits included.

In another preferred embodiment of the invention, no zeolitic structure other than the faujasite structure, preferably no zeolitic structure other than the faujasite Y structure is detected by X-ray diffraction in the agglomerated zeolitic adsorbent of the invention.

By «no», it is meant less than 5 weight %, preferably less than 2 weight % of zeolite structure other than FAU structure relative to the total weight of the adsorbent, the weight fractions being determined by XRD.

In addition, it is preferred that the weight fraction of FAU zeolite, and preferably the weight fraction of FAU-Y zeolite, is higher than or equal to 80% relative to the total weight of agglomerated zeolitic adsorbent of the invention, the remainder up to 100% preferably being composed of non-zeolitic phase i.e. a non-crystalline phase that is essentially inert against adsorption.

The agglomerated zeolitic adsorbent of the invention comprises one or more cations, preferably alkali or alkaline-earth, more preferably selected from among lithium, sodium, barium, calcium and potassium, alone or mixtures of two or more thereof, and most preferably selected from among lithium, sodium and calcium, alone or in mixtures of two or more thereof.

In one preferred embodiment, the content of sodium oxide ($Na_2O$) in the agglomerated zeolitic adsorbent of the invention is higher than 5%, more preferably higher than 8%, further preferably higher than 10% by weight relative to the total weight of the adsorbent, and advantageously said sodium oxide content is between 10% and 17%, and typically between 11% and 13% limits included, relative to the total weight of the adsorbent.

In another preferred embodiment, the content of potassium oxide ($K_2O$) in the agglomerated zeolitic adsorbent of the invention is lower than 12%, preferably lower than 5%, more preferably between 0 and 3%, further preferably between 0 and 2% by weight limits included, relative to the total weight of the adsorbent.

In another preferred embodiment, the content of calcium oxide (CaO) in the agglomerated zeolitic adsorbent of the invention is lower than 6%, preferably lower than 5%, more preferably between 0 and 4%, further preferably between 0 and 3% by weight limits included, relative to the total weight of the adsorbent.

In one embodiment of the invention, the zeolitic adsorbent may have a barium content lower than 6%, preferably between 0 and 4% limits included, expressed in weight of barium oxide BaO relative to the total weight of the adsorbent.

In one embodiment of the invention, the zeolitic adsorbent nay have a lithium content lower than 8%, preferably between 0 and 4% limits included expressed in weight of lithium oxide $Li_2O$ relative to the total weight of the adsorbent.

In another embodiment of the invention, the total content of cations other than lithium, sodium, potassium, calcium and barium is generally lower than 2% and most often between 0 and 1% limits included, this total content being expressed in weight of oxides of said cations relative to the total weight of the zeolitic adsorbent.

In one embodiment of the present invention, the loss on ignition of the agglomerated zeolitic adsorbent of the invention, measured at 900° C. according to standard NF EN 196-2, is less than or equal to 7° A), preferably between 0 and 6%, more preferably between 0 and 4% further preferably between 0 and 3% and advantageously between 0 and 2.5%, limits included.

In another aspect, the present invention concerns the use of the agglomerated zeolitic adsorbent such as just described, in processes:

- to separate C8 aromatic isomer fractions and xylenes in particular, and more particularly meta-xylene;
- to separate isomers of substituted toluene such as nitrotoluene, diethyltoluene, toluenediamine, and others;
- to separate cresols,
- to separate polyhydric alcohols.

Finally, in a further aspect, the present invention concerns the process for separating meta-xylene from aromatic isomer fractions having 8 carbon atoms, using as meta-xylene adsorption agent an agglomerated zeolitic adsorbent such as previously defined and more specifically in the remainder hereof, in liquid phase or in gas phase.

The process of the invention for separating meta-xylene from isomer fractions of aromatic hydrocarbons having 8 carbon atoms is preferably conducted in liquid phase via adsorption of meta-xylene in the presence of a desorbent, said desorbent possibly being any desorbent known to skilled persons and in particular any desorbent having a boiling point lower than that of the feed, such as toluene or indane, but also a desorbent having a boiling point higher than that of the feed, such as tetralin.

In one preferred embodiment, the meta-xylene separation process of the invention is a process of simulated moving bed type, more preferably of simulated counter-current type.

DETAILED DESCRIPTION OF EMBODIMENTS

The zeolitic adsorbent of the invention preferably comprises macropores, mesopores as well as micropores. By «macropores», it is meant pores having an opening greater than 50 nm, preferably between 50 nm and 400 nm. By «mesopores», it is meant pores having an opening of between 2 nm and 50 nm, limits not included. By «micropores», it is mean pores having an opening smaller than 2 nm.

As previously indicated, the adsorbent of the present invention is in the form of an adsorbent having particle porosity of between 25% and 45%, preferably between 30% and 45%, more preferably between 32% and 45%, further preferably between 35% and 45%, and particularly advantageously between 36% and 45% limits included. Also, the standard deviation σ of crystal size distribution in said adsorbent is less than 0.30 μm, preferably between 0.05 μm and 0.30 μm, more preferably between 0.05 μm and 0.28 μm, further preferably between 0.10 μm and 0.28 μm, and most preferably between 0.10 μm and 0.25 μm, limits included.

The inventors have surprisingly discovered that when the standard deviation σ of crystal size distribution in the zeolitic adsorbent is greater than 0.3 μm, a drastic drop in productivity is observed in a meta-xylene separation process, in particular in a liquid phase separation process in a simulated counter-current moving bed.

It was additionally surprisingly observed that this productivity value reaches a maximum with values of standard deviation σ of crystal size distribution in the zeolitic adsorbent agglomerate of less than 0.3 μm. This standard deviation σ value appears to correspond to optimized particle porosity. It was also observed in fully surprising manner that particle porosity is inversely proportional to the standard deviation σ of crystal size distribution in the zeolitic adsorbent agglomerate. Therefore, the more the standard deviation σ decreases, the more particle porosity increases. Yet, particle porosity that is too high leads to fully undesirable effects, such as loss of adsorption capacity for example, loss of mechanical strength, and others.

As a result, with the invention, persons skilled in the art desiring maximum productivity will find a trade-off between particle porosity and the standard deviation σ of crystal size distribution in the zeolitic adsorbent agglomerate. With the agglomerated adsorbent of the invention it is thus possible to obtain maximum productivity in xylene separation processes, in particular for the separation of meta-xylene.

Advantageously, the agglomerated zeolitic adsorbent is in the form of beads of mean diameter between 100 μm and 1000 μm, preferably between 100 μm and 600 μm, more preferably between 200 μm and 550 μm, limits included.

Preferably, the faujasite zeolitic adsorbent of the invention comprises sodium or lithium or calcium or a mixture of two or the three thereof.

Preferably, the zeolitic adsorbent of the present invention contains FAU zeolite(s), generally referenced under the name zeolite of type Y. By «zeolite Y», it is meant a zeolite having a Si/Al atomic ratio of between 1.5 and 6.0 limits excluded, as previously indicated.

The zeolitic adsorbent agglomerates of the present invention can contain a non-zeolitic phase (NZP) i.e. a non-crystalline phase which is essentially inert against adsorption. The crystallinity content (weight fraction of zeolite) of the adsorbent of the invention can be measured by X-ray diffraction analysis known to skilled persons under the abbreviation XRD.

The zeolitic adsorbent agglomerate of the invention is preferably in the form of an agglomerate i.e. it is composed of crystalline elements (or crystals) of at least one FAU zeolite such as previously defined, said crystalline elements (or more simply «crystals») preferably having a number-weighted mean diameter of less than 1200 nm, preferably between 100 nm and 1200 nm, more preferably between 400 nm and 1200 nm, further preferably between 500 nm and 1200 nm, still further preferably between 550 nm and 1200 nm, and most advantageously between 600 nm and 1200 nm, limits included.

The zeolitic adsorbent agglomerates of the invention can be prepared by adapting operating modes already known to persons skilled in the art, as described for example in documents US2009326308, U.S. Pat. No. 10,125,064, TW201107032 and US2007224113, and by selecting and adjusting the synthesis parameters allowing agglomerates to be obtained having the desired values of particle porosity and standard deviation σ.

A process for synthesizing the zeolitic adsorbent agglomerate of the present invention may, for example, comprise at least the steps of:

a) agglomerating crystals of at least one zeolite of FAU-Y type with a binder comprising at least 80% of clay or mixture of zeolitizable clays, optionally with up to 5% of additives, and with an amount of water allowing the forming of the agglomerate material; drying the agglomerates at a temperature of between 50° C. and 150° C.; calcining the dried agglomerates under an oxidizing and/or inert purge gas in particular with gases such as oxygen, nitrogen, air, dry and/or decarbonated air, oxygen-depleted air optionally dry and/or decarbonated, at a temperature higher than 150° C., typically between 180° C. and 800° C., preferably between 200° C. and 650° C.;

b) optionally zeolitizing all or part of the binder by contacting the agglomerates obtained at step a) with am alkaline base solution;

c) optional cationic exchanges(s) of the agglomerates of step a) and/or step b) by contacting with one of more cation solutions, simultaneously or sequentially;

d) washing and drying the agglomerates obtained at step c), at a temperature of between 50° C. and 150° C.; and e) activation by heating to a temperature generally of between 100° C. and 400° C., preferably between 200° C. and 300° C. followed by recovery of the zeolitic agglomerated adsorbent.

The zeolite crystals able to be used at synthesis step a) above can advantageously be synthesized following known operating modes available in the scientific literature or patent literature, and on the internet. In particular the zeolite crystals can be prepared as described in documents U.S. Pat No. 10,071,914 and US2007224113.

The parameters allowing control over the standard deviation σ in the zeolitic adsorbent agglomerate of the present invention are for example related to the type of crystals used at step a), in particular the size and standard deviation of said crystals, but also the zeolitization conditions of the agglomerating binder e.g. temperature, time, pH of the alkaline zeolitization solution, as well as duration, agitation mode, shear rate, pressure and others.

More specifically, by «type of crystals used at step a)», it is particularly meant the standard deviation of said crystals which can be controlled for example by adjusting the synthesis parameters and in particular synthesis temperature, agitation speed, shear rate as indicated for example in documents WO2009081022 or US2009326308.

The synthesis parameters allowing control over the porosity of the zeolitic adsorbent agglomerate of the invention are also known to skilled persons. In general, these parameters comprise but are not limited thereto, the binder percentage, type of agglomeration (by extrusion, atomization, granulation, etc.), humidity level, type of binder, zeolitization conditions (temperature, time, pH of the alkaline zeolitization solution, duration, agitation mode, shear rate, pressure and others).

In one preferred embodiment, the synthesis of the zeolitic adsorbent agglomerate of the present invention does not comprise the addition of a pore-forming agent, the presence of a pore-forming agent possibly leading to degradation of crystallinity in particular.

It is also possible to prepare said crystalline elements by synthesis via seeding and/or adjustment of synthesis operation conditions such as $SiO_2/Al_2O_3$ ratio, sodium content and alkalinity of the synthesis mixture.

The synthesis of zeolite of FAU type is generally conducted in a sodium medium ($Na^+$ cation). The crystalline elements of FAU zeolite thus obtained mostly even exclusively contain sodium cations. It would remain within the scope of the invention however to use crystalline elements having undergone one or more cationic exchanges between synthesis in sodium form.

The size of the FAU zeolite crystals used at step a) and of the crystalline elements of FAU zeolite in the agglomerates of the invention is measured under scanning electron microscopy (SEM). As previously indicated, preferably the mean diameter of the crystals is generally less than 1200 nm, preferably between 100 nm and 1200 nm, more preferably between 400 nm and 1200 nm, further preferably between 500 nm and 1200 nm, still further preferably between 550 nm and 1200 nm, and most advantageously between 600 nm and 1200 nm, limits included.

This SEM observation also allows confirmation of the presence of a non-zeolitic phase, for example comprising residual binder (not converted at the zeolitization step) or any other amorphous phase in the agglomerates.

In the present document, the term «number-weighted mean diameter» is used or else «size», in particular for the crystalline zeolite elements and for the zeolitic adsorbents. The measuring method of these magnitudes is explained later in the description.

The agglomeration and forming (step a) can be performed using any technique known to skilled persons, such as extrusion, compacting, agglomeration on plate granulator, drum granulator, atomization and others.

The proportions of agglomerating binder (see definition below) and of zeolite used are typically those of the prior art i.e. 5 parts to 20 parts by weight of binder per 95 parts to 80 parts by weight of zeolite.

The agglomerates derived from step a), whether in the form of beads, extrudates or other, generally have a number-weighted mean diameter, or length (longest dimension when they are not spherical) of between 0.1 mm and 1 mm, and in particular between 0.1 mm and 0.6 mm and preferably between 0.2 mm and 0.55 mm, limits included.

After step a), the finest agglomerates can be removed by cyclone removal and/or screening, and/or the agglomerates that are too large by screening or crushing in the case of extrudates for example.

The binder included in the zeolitic agglomerated material of the present invention comprises and preferably consists of a clay or mixture of clays. These clays are preferably selected from among kaolins, kaolinites, nacrites, dickites, halloysites, attapulgites, sepiolites, montmorillonites, bentonites, illites and metakaolins, and the mixtures of two or more thereof in any proportion.

For the zeolitization step, the agglomerating binder used at step a) contains at least 80% preferably at least 90%, more preferably at least 95%, more particularly at least 96% by weight of at least one zeolitizable clay and may also contain other mineral binders such as bentonite, attapulgite, and others. By zeolitizable clay, it is meant a clay or mixture of clays able to be converted to zeolitic material, most often through the action of an alkaline base solution. The zeolitizable clay generally belongs to the kaolin family (e.g. kaolinites, nacrites, dickites, halloysites) and/or metakaolins.

Among the additives optionally used at step a), these may include a silica source of any type known to skilled persons, specialists in the synthesis of zeolites, e.g. colloidal silica, diatoms, perlite, fly ash, sand, or any other form of solid silica.

At step a), in addition to the crystalline elements of FAU zeolite and binder, other additives can also be used e.g. additives intended to facilitate agglomeration or improve hardening, and other additives known to skilled persons.

In particular, if the agglomerating binder contains one or more zeolitizable clays, calcining allows the conversion of zeolitizable clay, typically kaolin, to meta-kaolin which can then be converted to zeolite at the zeolitization step (step b)). The principle thereof is set forth in «*Zeolite Molecular Sieves*» by D. W. Breck, John Wiley and Sons, New York, (1973), p. 314-315.

Optional zeolitization of the agglomerating binder is performed using any method currently well known to skilled persons, and for example can be performed by immersion of the product derived from step a) in an alkaline base solution, generally aqueous, for example an aqueous solution of sodium hydroxide and/or potassium hydroxide.

As a general rule, the concentration of the alkaline zeolitization solution is preferably between 0.5 M and 5 M. Zeolitization is preferably conducted under heat at a temperature higher than ambient temperature, and typically at temperatures in the region of 80° C. to 100° C. The duration of the zeolitization process is generally between a few tens of minutes and a few hours, preferably between about 1 hour and 8 hours.

Preferably, and to ensure full zeolitization of the binder without deteriorating the crystallinity of the zeolite crystals present, it is preferred to contact the adsorbents with a cold sodium hydroxide solution and to apply a gradual temperature rise up to a temperature of 80° C.-100° C.

Similarly, the concentration of sodium hydroxide can be maintained at the same concentration or it can be gradually increased to maintain maximum crystallinity of the initial crystals and to ensure maximum conversion of the zeolitizable binder.

The optional cationic exchange step(s) are performed according to conventional methods known to skilled persons, and most often by contacting the agglomerates derived from step a) with a salt of the cation(s) corresponding to the desired cationic exchange. The cationic exchange operation is generally conducted in an aqueous solution at a temperature between ambient temperature and 100° C., and preferably at between 80° C. and 100° C.

It is preferred to operate with a large molar excess of aqueous solution of the desired cation relative to the cations of the zeolite it is desired to exchange, advantageously proceeding via successive exchanges to obtain the desired rate of exchange.

After the cationic exchange step(s), washing is carried out generally and preferably with water followed by drying of the agglomerate thus obtained.

Activation which follows after drying is conducted in conventional manner using methods known to skilled persons e.g. at a temperature in general of between 100° C. and 400° C., preferably between 200° C. and 300° C. for a determined time as a function of desired water content and loss on ignition, typically from 1 hour to 6 hours.

CHARACTERIZATION TECHNIQUES

Particle Size Measurement of the Zeolite Crystals

Estimation of the number-weighted mean diameter of the elements (i.e. crystals) of FAU type zeolite used at step a) and of the elements (i.e. crystals) of zeolite Y contained in the agglomerates is performed by observation under scanning electron microscopy (SEM).

To estimate the size of the particles (i.e. crystals) of zeolite in samples, a set of images is taken with magnification of at least 5000. The diameter is then measured of at least 200 particles using dedicated software e.g. Smile View software by LoGraMi. Accuracy is in the region of 3%. Measurement of the histogram formed from said diameter measurements allows the standard deviation σ of the distribution thereof to be determined at the same time.

Chemical Analysis of the Zeolitic Adsorbent Agglomerates—Si/Al Ratio and Rate of Exchange Elementary chemical analysis of the end product obtained after steps a) to e) previously described, can be carried out using different analytical techniques known to skilled persons. Among these techniques, mention can be made of X-ray fluorescence chemical analysis such as described in standard NF EN ISO 12677:2011 on a wavelength dispersive X-ray fluorescence spectrometer (WDXRF), e.g. Tiger S8 by Bruker.

X-ray fluorescence is a non-destructive spectral technique using the photoluminescence of atoms in the X-ray domain to determine the elementary composition of a sample. Excitation of the atoms, generally by an X-ray beam or electron bombardment, generates specific radiation after return to the fundamental state of the atom. The spectrum of X-ray fluorescence has the advantage of being very scarcely dependent on the chemical combination of the element, which affords precise determination both quantitative and qualitative. After calibration, the measurement uncertainty obtained for each oxide is conventionally less than 0.4 weight %.

These elementary chemical analyses allow verification of both the Si/Al atomic ratio of the zeolite used in the agglomerate and the Si/Al atomic ratio of the end product obtained after steps a) to e) previously described, as well as verification of the quality of the ionic exchange described at step c). In the description of the present invention, the measurement uncertainty of the Si/Al atomic ratio is ±5%.

Quality of ionic exchange is related to the number of moles of sodium oxide, $Na_2O$, remaining in the zeolitic agglomerate after exchange. More specifically, the rate of exchange by a cation is estimated by evaluating the ratio between the number of moles of oxide of said cation and the number of moles of all the other oxides of cations that are present.

For example, for a zeolitic adsorbent agglomerate containing sodium and lithium cations, the rate of exchange of the lithium cation is estimated by evaluating the ratio between the number of moles of lithium oxide $Li_2O$, and the number of moles of the group $(Li_2O+Na_2O)$.

It is to be noted that the contents of the different oxides are given in weight percentage relative to the total weight of the anhydrous zeolitic adsorbent.

Particle Size Measurement of the Zeolitic Adsorbents

Determination of the number-weighted mean diameter of the zeolitic adsorbents obtained after the agglomeration and forming step a), is carried out by analysis of particle size distribution in a sample of agglomerate via imaging according to standard ISO 13322-2:2006, using a conveyor allowing the sample to pass in front of the camera.

The number-weighted mean diameter is then calculated from particle size distribution by applying standard ISO 9276-2:2001. In the present document, the term «number-weighted mean diameter» is used or else «size» for the zeolitic agglomerates. Accuracy is in the region of 0.01 mm for the size range of the agglomerates of the invention.

Mechanical Strength of the Zeolitic Adsorbents

The crushing strength of a bed of zeolitic adsorbents such as described in the present invention is characterized by the Shell Method Series SMS1471-74 «Determination of Bulk Crushing Strength of Catalysts. Compression-Sieve Method», associated with «BCS Tester» apparatus marketed by Vinci Technologies. This method, initially intended for characterization of catalysts of 3 mm to 6 mm, is based on the use of a 425 μm screen allowing separation of the fines at the time of crushing. The use of a 425 μm screen remains suitable for particles of diameter greater than 1.6 mm, but must be adapted to the particle size of the agglomerates it is sought to characterize The agglomerates of the present invention, generally in the form of beads or extrudates, generally have a number-weighted mean diameter or length i.e. longest dimension for non-spherical agglomerates, of between 0.2 mm and 2 mm, and in particular between 0.1 mm and 1.0 mm, preferably between 0.1 mm and 0.6 mm, limits included. Consequently, a 100 µm screen is used instead of the 425 µm screen mentioned in Shell standard SMS1471-74.

The protocol for measurement is as follows: a 20 cm³ sample of agglomerated adsorbents, previously screened with the adapted screen (100 µm) and previously oven-dried for at least 2 hours at 250° C. (instead of 300° C. mentioned in Shell standard SMS1471-74), is placed in a metal cylinder of known internal cross-section. An increasing force is applied in incremental stages on this sample via a piston, through a 5 cm³ bed of stainless-steel beads for better distribution of the force applied by the piston on the adsorbent agglomerates (use of beads 2 mm in diameter for particles of spherical shape having a diameter of strictly less than 1.6 mm). The fines obtained at the different incremental stages of applied pressure are separated by screening (adapted 100 µm screen) and weighed.

In-bed crushing strength is determined by the pressure in megaPascals (MPa) at which the quantity of accumulated fines passing through the screen amount to 0.5 weight % of the sample. This value is obtained by plotting on a graph the mass of fines obtained as a function of the force applied to the bed of adsorbent and interpolating 0.5 weight % of accumulated fines. The in-bed crushing strength is typically between a few hundred kPa and a few tens of MPa and is generally between 0.3 MPa and 3.2 MPa. Accuracy is conventionally to within less than 0.1 MPa.

Non-Zeolitic Phase of the Zeolitic Adsorbents

The percentage of non-zeolitic phase NZP, e.g. residual non-zeolitized binder or any other amorphous phase, after zeolitization, is calculated with the following equation:

NZP=100−Σ(ZP)

where ZP represents the sum of the quantities of zeoliteY fractions in the meaning of the invention.

The percentage of zeolite Y fractions (percent crystallinity) is measured by X-ray diffraction analysis known to skilled persons under the abbreviation XYD. This analysis is carried out on Bruker apparatus and the percentage of zeolite Y fractions is evaluated with TOPAS software by Bruker.

Micropore Volume

The crystallinity of the agglomerates is also evaluated by measuring the micropore volume thereof by comparing the latter with that of an appropriate reference (100% crystalline zeolite under same cationic treatment conditions, or theoretical zeolite). This micropore volume is determined from measurement of the gas adsorption isotherm, e.g. nitrogen, at the liquefying temperature thereof.

Prior to adsorption, the zeolitic adsorbent is degassed at between 300° C. and 450° C. for a time of between 9 hours and 16 hours, in a vacuum ($P<6.7\times10^{-4}$ Pa). Measurement of the nitrogen adsorption isotherm at 77 K is then performed on apparatus of type ASAP 2020 M by Micromeritics, taking at least 35 measurement points at relative pressures with a $P/P_0$ ratio of between 0.002 and 1.

Total Volume of Macropores and Mesopores

Macropore Vma and mesopore Vme volumes, particle density Dp and porosity $\varepsilon_p$ of macroporosity and mesoporosity type, are measured by mercury intrusion porosimetry. A mercury porosimeter of Autopore® 9500 type by Micromeritics is used to analyse the distribution of pore volume in the macropores and mesopores.

The experimental method described in the operating manual of the apparatus with reference to standard ASTM D4284-83, consists of placing a sample of adsorbent, (zeolitic adsorbent in agglomerate form to be measured) of known loss on ignition and previously weighed, in a porosimeter cell and after prior degassing (evacuation pressure of 30 µm mercury for at least 10 min), filling the cell with mercury at a given pressure (0.0036 MPa) and then applying increasing levels of pressure up to 400 MPa to cause the mercury gradually to enter the porous network of the sample, using at least 15 pressure levels up to 0.2 MPa, and then applying increments of 0.1 MPa up to 1 MPa, then 0.5 MPa up to 10 MPa, then 2 MPa up to 30 MPa, then 5 MPa up to 180 MPa, and finally 10 MPa up to 400 MPa.

The relationship between applied pressure and characteristic dimension of the pore entry threshold (corresponding to an apparent pore diameter) is determined using the Laplace-Young equation and assuming a cylindrical pore opening, a contact angle between mercury and the pore walls of 140° and mercury surface tension of 485 dynes cm$^{-1}$. The volume increments ΔVi of mercury inserted at each pressure level Pi are recorded, allowing subsequent plotting of the accumulated volume of inserted mercury as a function of applied pressure V(Pi), or as a function of the apparent diameter of the pores V(li). The value on and after which the mercury fills all inter-particle voids is set at 0.2 MP, and it is considered that above this value the mercury enters into the pores of the adsorbent. The particle volume Vp is then calculated by subtracting the accumulated volume of mercury at this pressure (0.2 MPa) from the volume of the porosimeter cell, and dividing this difference by the mass of equivalent anhydrous adsorbent i.e. the mass of said material corrected for loss on ignition. Particle density Dp is the inverse of particle volume Vp previously defined.

The macropore volume Vma of the adsorbent is defined as the accumulated volume of mercury inserted at a pressure of between 0.2 MPa and 30 MPa, corresponding to the volume contained in the pores of apparent diameter greater than 50 nm. The mesopore volume Vme of the adsorbent is defined as being the accumulated volume of mercury inserted at a pressure of between 30 MPa and 400 MPa. Since the method for measuring pore volume via mercury intrusion does not afford access to micropore volume, the total pore volume Vtot such as measured by mercury intrusion corresponds to the sum of the macropore Vma and mesopore Vme volumes.

In the present document, the macropore and mesopore volumes Vma and Vme, and the sum thereof (total pore volume Vtot), of the zeolitic adsorbents, expressed in cm³ g$^{-1}$, are therefore measured by mercury intrusion porosimetry and related to the mass of the sample in anhydrous equivalent i.e. the mass of said adsorbent corrected for loss on ignition. Particle density Dp is expressed in g cm$^{-3}$ and refers to the mass of the sample in anhydrous equivalent.

Porosity $\varepsilon_p$ of macroporosity and mesoporosity type, is the product of particle density Dp multiplied by the sum of the macropore and mesopore volumes Vma and Vme:

$$\varepsilon p = Dp \times (Vma+Vme)$$

Loss on Ignition of the Zeolitic Adsorbents

Loss on ignition is determined in an oxidizing atmosphere, by calcining the sample in air at a temperature of 900° C.±25° C., following the operating mode described in standard NF EN 196-2 (April 2006). The standard deviation of measurement is less than 0.1%.

EXAMPLES

Example 1: Preparation of the Agglomerates

Two agglomerated adsorbents are prepared: Agglomerate 1 (according to the invention), and Agglomerate 2, as comparative example. Both agglomerates are prepared as shown below from NaY faujasite type zeolite crystals, the mean size of which is 0.5 µm. The standard deviations of these crystals are 0.23 µm and 0.60 µm respectively.

Preparation of Agglomerate 1 (according to the invention)

800 g of NaY zeolite crystals (standard deviation 0.23 µm), 160 g kaolin clay (expressed as calcinated equivalent), and 195 g of commercial colloidal silica Klebosol™ 30N50 (containing 30 wt % SiO2 and 0.5 wt % Na2O) are homogeneously mixed and agglomerated with water allowing extrusion of the mixture. The extrudates are dried and calcined at 550° C. (firing of the clay) under nitrogen flow during 2 hours, and then grounded so as to obtain agglomerates of number mean diameter equal to 0.5 mm.

The so obtained agglomerates (20 g) are placed into a double jacket glass reactor and maintained at a temperature of 90° C.±1° C. then 275 mL of 1.0 M aqueous solution of sodium hydroxide is then added and the reaction medium is agitated at this temperature during 3.5 hours.

The agglomerates are then successively washed 3 times with water and the reactor is emptied. The efficacy of the washing is assessed with the control of the final pH of the wash waters, which is between 10.0 and 10.5.

The agglomerates are then dried at 80° C. during 2 hours and then activated at 400° C. during 2 hours under nitrogen flow.

Preparation of Agglomerate 2 (comparative example)

800 g of NaY zeolite crystals (standard deviation 0.60 µm), 145 g kaolin clay (expressed as calcinated equivalent), and 180 g of commercial colloidal silica Klebosol™ 30N50 (containing 30 wt % SiO2 and 0.5 wt % Na2O) are homogeneously mixed and agglomerated with water so that the mixture can be extruded. The extrudates are dried and calcined at 550° C. (clay firing) under nitrogen flow during 2 hours, and then grounded so as to obtain agglomerates of number mean diameter equal to 0.5 mm.

The so obtained agglomerates (20 g) are placed into a double jacket glass reactor and maintained at a temperature of 95° C.±1° C. then 275 mL of an 1.15 M aqueous solution of sodium hydroxide is then added and the reaction medium is agitated at this temperature during 3 hours.

The agglomerates are then successively washed 3 times with water and the reactor is emptied. The efficacy of the washing is assessed with the control of the final pH of the washwaters, which is between 10.0 and 10.5.

The agglomerates are then dried at 80° C. during 2 hours and then activated at 400° C. during 2 hours under nitrogen flow.

Characteristics of Agglomerate 1 and Agglomerate 2

The values of particle porosity εp as well as the standard deviations σ of the crystals in the final agglomerates, for Agglomerate 1 and Agglomerate 2 are indicated in the Table 1 below.

The mean size of the NaY crystals, as measured in the final Agglomerate 1 is 0.71 µm, and the mean size of the NaY crystals, as measured in the final Agglomerate 2 is 0.65 µm.

The Loss on ignition is measured as described above and is 2.5%±0.1%

Example 2: Breakthrough Test Using Agglomerate 1 and Agglomerate 2

A breakthrough test (frontal chromatography) is performed using Agglomerate 1 and Agglomerate 2. The mentioned analysis allows assessing their respective separation efficiencies. The agglomerate amounts used for each of the tests are about 26 g.

The breakthrough curves are obtained according to the following method:

Filling the column with the agglomerate and setting the column in the equipment;

Filling the column with the solvent at ambient temperature;

Progressively heating under solvent flow (5 cm$^3$.min$^{-1}$) till the adsorption temperature is reached;

Setting the solvent injection at a rate of 30 cm$^3$.min$^{-1}$ once the adsorption temperature is reached.

Switching from the solvent to the feed lines in order to inject the feed flow (30 cm$^3$.min$^{-1}$);

Maintaining the feed flow injection during a sufficiently long time period in order to reach the thermodynamic equilibrium (i.e. until the solvent concentration in the effluent is zero);

Collecting and analyzing the effluent.

The solvent used is para-diethylbenzene. The feed is composed of:

Meta-xylene: 45 wt %

Ortho-xylene: 45 wt %

Iso-octane: 10 wt % (inert compound from the separation point of view used here only for tracing purposes in order to estimate the non-selective volumes)

The test is performed at 140° C. The pressure level is high enough to avoid fluid vaporization, i.e. 1 MPa. The superficial speed (flow rate/column section) of the liquid flow at the experimental temperature is about 1.2 cm·s$^{-1}$ for all the experiments.

The selectivity between Meta-xylene (MX) and Ortho-xylene (OX) ($\alpha$MX/OX) is calculated from the adsorbed volumes qMX and qOX of the compounds MX and OX (these ones being determined from the mass balance established by means of the analysis of the column effluent) as well as from the inlet feed composition, in which the volume fraction of the compounds is yMX and yOX):

$$\alpha_{MX/OX} = \frac{q_{MX}}{q_{OX}} \frac{y_{OX}}{y_{MX}}.$$

The obtained results are gathered in Table 1 below:

TABLE 1

| Adsorbent | Particle porosity ε$_p$ (%) | Standard deviation σ (µm) | MX/OX selectivity | Adsorption capacity (%) | HETP MX (%) |
|---|---|---|---|---|---|
| Agglomerate 1 (invention) | 36 | 0.19 | 1.83 | 13.3 | 8.63 |

TABLE 1-continued

| Adsorbent | Particle porosity $\varepsilon_p$ (%) | Standard deviation $\sigma$ (μm) | MX/OX selectivity | Adsorption capacity (%) | HETP MX (%) |
|---|---|---|---|---|---|
| Agglomerate 2 (comparative) | 27 | 0.35 | 1.84 | 13.2 | 10.2 |

Key
Adsorption capacity expressed in % (cm3 of adsorbed C8-aromatic compounds for 100 cm³ of column)
HETP = Height Equivalent to a Theoretical Plate as measured for meta-xylene (expressed as % of column length)
MX = Meta-Xylene; OX = Ortho-Xylene The results of these experiments show that the use of an agglomerated adsorbent according to the invention allows for a drastic reduction of the Height Equivalent to a Theoretical Plate (HEPT) measured for meta-xylene. This is a clear indication of an improvement of the mass transfer capacity. The separation process productivity being directly proportional to the mass transfer capacity improvement.

The invention claimed is:

1. An agglomerated zeolitic adsorbent, comprising at least one faujasite zeolite of atomic ratio Si/Al higher than 1.50, wherein particle porosity of the adsorbent is between 25% and 45%, limits included, and wherein standard deviation o of crystal size distribution in the agglomerated zeolitic adsorbent is less than 0.30 μm.

2. The agglomerated zeolitic adsorbent according to claim 1, wherein the adsorbent comprises zeolite crystals having a number-weighted mean diameter less than 1200 nm.

3. The agglomerated zeolitic adsorbent according to claim 1, the adsorbent is in the form of beads of a mean diameter between 100 μm and 1000 μm, limits included.

4. The agglomerated zeolitic adsorbent according to claim 1, wherein the at least one faujasite zeolite has a Si/Al atomic ratio of between 1.50 and 6.50, limits excluded.

5. The agglomerated zeolitic adsorbent according to claim 1, comprising one or more cations.

6. The agglomerated zeolitic adsorbent according to claim 1, wherein the adsorbent comprises sodium oxide ($Na_2O$) in a content higher than 5% by weight relative to the total weight of the adsorbent.

7. The agglomerated zeolitic adsorbent according to claim 5, wherein the total content of cations other than lithium, sodium, potassium, calcium and barium is less than 2%, this total content being expressed in weight of oxides of the cations relative to the total weight of the zeolitic adsorbent.

8. The agglomerated zeolitic adsorbent according to claim 1, wherein no zeolitic structure other than the faujasite structure is detected by X-ray diffraction.

9. The agglomerated zeolitic adsorbent according to claim 1, wherein the weight fraction of the at least one faujasite zeolite is higher than or equal to 80% relative to the total weight of the adsorbent.

10. A process for using an agglomerated zeolitic adsorbent according to claim 1, where the process is chosen from the following:
separating C8 aromatic isomer fractions;
separating isomers of substituted toluene;
separating cresols;
separating polyhydric alcohols.

11. The process according to claim 10, wherein meta-xylene is separated from aromatic isomer fractions having 8 carbon atoms.

12. A process for separating meta-xylene from aromatic isomer fractions having 8 carbon atoms, by contacting the aromatic isomer fractions with the agglomerated zeolitic adsorbent according to claim 1, in a liquid phase or in a gas phase.

13. The process according to claim 12, where the process takes place in a liquid phase via adsorption of the meta-xylene in the presence of a desorbent.

14. The process according to claim 12, where the process is performed in a simulated moving bed type.

* * * * *

UNITED STATES PATENT AND TRADEMARK OFFICE
CERTIFICATE OF CORRECTION

PATENT NO. : 12,005,420 B2
APPLICATION NO. : 17/787351
DATED : June 11, 2024
INVENTOR(S) : Perez-Pellitero et al.

It is certified that error appears in the above-identified patent and that said Letters Patent is hereby corrected as shown below:

In the Claims

Column 17, Line 24, Claim 1: "deviation o" should read -- deviation $\sigma$ --.

Signed and Sealed this
First Day of October, 2024

Katherine Kelly Vidal
*Director of the United States Patent and Trademark Office*